US011839578B2

(12) United States Patent
Jones

(10) Patent No.: US 11,839,578 B2
(45) Date of Patent: Dec. 12, 2023

(54) BODILY WASTE COLLECTION USING PERIODIC PRESSURE

(71) Applicant: PureWick Corporation, El Cajon, CA (US)

(72) Inventor: Jill M. Jones, Atlanta, GA (US)

(73) Assignee: PUREWICK CORPORATION, Covington, GA (US)

( * ) Notice: Subject to any disclaimer, the term of this patent is extended or adjusted under 35 U.S.C. 154(b) by 87 days.

(21) Appl. No.: 17/494,578

(22) Filed: Oct. 5, 2021

(65) Prior Publication Data

US 2022/0104981 A1  Apr. 7, 2022

Related U.S. Application Data

(60) Provisional application No. 63/088,539, filed on Oct. 7, 2020.

(51) Int. Cl.
*A61G 9/00* (2006.01)

(52) U.S. Cl.
CPC ..................... *A61G 9/00* (2013.01)

(58) Field of Classification Search
CPC ....................................... A61G 9/00
See application file for complete search history.

(56) References Cited

U.S. PATENT DOCUMENTS

| 2009/0065412 | A1* | 3/2009 | Mbarki | C02F 3/2806 210/151 |
| 2011/0137273 | A1 | 6/2011 | Muellejans et al. | |
| 2014/0276501 | A1 | 9/2014 | Cisko | |
| 2017/0354906 | A1* | 12/2017 | Wu | C05F 17/05 |
| 2021/0188680 | A1* | 6/2021 | Kumkrong | B09B 5/00 |
| 2021/0330485 | A1 | 10/2021 | Sexton et al. | |
| 2022/0062023 | A1* | 3/2022 | Walthall | A61F 5/441 |
| 2022/0287867 | A1* | 9/2022 | Jones | A61F 5/4405 |

FOREIGN PATENT DOCUMENTS

| DE | 79818 C | 10/1893 |
| WO | 2007134608 A2 | 11/2007 |
| WO | 2017001846 A1 | 1/2017 |

OTHER PUBLICATIONS

U.S. Appl. No. 17/412,864, filed Aug. 26, 2021.
U.S. Appl. No. 63/033,310, filed Jun. 2, 2020.
U.S. Appl. No. 63/071,821, filed Aug. 28, 2020.
U.S. Appl. No. 63/088,539, filed Oct. 7, 2020.
U.S. Appl. No. 63/159,280, filed Mar. 10, 2021.

(Continued)

*Primary Examiner* — J C Jacyna
(74) *Attorney, Agent, or Firm* — DORSEY & WHITNEY LLP

(57) ABSTRACT

Examples relate to devices, systems, and methods for collecting bodily waste as well as separating the liquids from the solids in the bodily waste. The devices, systems, and methods disclosed herein utilize a bodily waste separation device having an at least semi-rigid tray, a lid fluidly sealed to the at least semi-rigid tray, an output manifold fluidly sealed to the at least semi-rigid tray, an intake configured to fluidly connect the interior region of the at least semi-rigid tray to a source outside of the separation device, and a filter disposed between the at least semi-rigid tray and the output manifold.

19 Claims, 6 Drawing Sheets

(56) References Cited

OTHER PUBLICATIONS

International Search Report and Written Opinion from International Application No. PCT/US2021/035181 dated Sep. 16, 2021.
Non-Final Office Action for U.S. Appl. No. 17/654,156 dated Apr. 10, 2023.
Restriction Requirement for U.S. Appl. No. 17/412,864 dated Apr. 19, 2023.
U.S. Appl. No. 17/654,156, filed Mar. 9, 2022.
U.S. Appl. No. 17/999,648, filed Nov. 22, 2022.

* cited by examiner

BODILY WASTE COLLECTION USING PERIODIC PRESSURE

CROSS-REFERENCE TO RELATED APPLICATIONS

This application claims priority to U.S. Provisional Patent Application No. 63/088,539 filed on 7 Oct. 2020, the disclosure of which is incorporated herein, in its entirety, by this reference.

BACKGROUND

An individual may have limited or impaired mobility such that bowel movements in a restroom are challenging or impossible. For example, the individual may have a condition, had a surgery, or a have disability that impairs mobility. In another example, the individual may have restricted travel conditions such as those experience by pilots, drivers, and workers in hazardous areas. Additionally, stool collection from the individual may be needed for monitoring purposes or clinical testing.

Bed pans and ostomy bags, may be used to address some of these circumstances. However, bed pans and ostomy bags have several problems associated therewith. For example, bed pans may be prone to discomfort, spills, and other hygiene issues. Ostomy bags require intrusive surgery. For example, using ostomy bags requires a surgical procedure to make an ostomy and stoma to connect to the ostomy bag, which may be painful, prone to infections, and leave permanent scarring or other side effects.

Thus, users and manufacturers of stool collection devices continue to seek new and improved devices, systems, and methods to collect stool.

SUMMARY

Embodiments disclosed herein are related to devices, systems, and methods for collecting bodily waste as well as separating the liquids from the solids in the bodily waste.

In an embodiment, a bodily waste separation device is disclosed. The bodily waste separation device includes an at least semi-rigid tray. The tray of the bodily waste separation device includes at least semi-rigid outer walls defining an interior region, the outer walls having an upper end and a lower end. The tray of the bodily waste separation device includes a plurality of dividers disposed consecutively within the interior region to form a plurality of chambers arranged consecutively between the outer walls. The bodily waste separation device includes a lid fluidly sealed to an upper end of the outer walls. The bodily waste separation device includes an intake configured to fluidly connect the interior region to a bodily waste collection device. The bodily waste separation device includes an output manifold fluidly sealed to the outer walls at the lower end, the output manifold including one or more drainage ports configured to fluidly connect to one or more drainage tubes. The bodily waste separation device includes a filter disposed between the lower end of the outer walls and the output manifold.

In an embodiment, a bodily waste collection system is disclosed. The bodily waste collection system includes a fluid storage container configured to hold a fluid. The bodily waste collection system includes a bodily waste separation device fluidly connected to the fluid storage container. The bodily waste separation device of the system includes an at least semi-rigid tray, the tray including at least semi-rigid outer walls defining an interior region, the outer walls having an upper end and a lower end and a plurality of dividers disposed consecutively within the interior region to form a plurality of chambers arranged consecutively between the outer walls. The bodily waste separation device includes at least semi-rigid tray includes a lid fluidly sealed to an upper end of the outer walls. The bodily waste separation device includes an intake configured to fluidly connect the interior region to a bodily waste collection device. The bodily waste separation device includes an output manifold fluidly sealed to the outer walls at the lower end, the output manifold including one or more drainage ports configured to fluidly connect to one or more drainage tubes. The bodily waste separation device includes a filter disposed between the lower end of the outer walls and the output manifold. The bodily waste collection system includes a vacuum source fluidly connected to one or more of the fluid storage container or the bodily waste separation device, the vacuum source configured to apply a vacuum to draw fluid from the interior region.

In an embodiment, a method to collect bodily waste is disclosed. The method includes receiving bodily waste from a patient into one or more of a plurality of chambers of a bodily waste separation device, the bodily waste including liquid and solids. The method includes filtering liquid from the bodily waste in the one or more of the plurality of chambers. The method includes removing the filtered liquid from the bodily waste separation device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to devices, systems, and methods for collecting bodily waste as well as separating the liquids from the solids in the bodily waste. The liquids may be removed from the separation device while the solids are retained. The bodily waste collection apparatuses disclosed herein includes a plurality of chambers arranged consecutively. Each chamber is connected to a filter to separate the liquids from the solids in the bodily waste. As a first chamber fills with solids or the filter in the first chamber clogs with solids, the waste introduced into the first chamber fills the first chamber and spills into the second chamber where the filter in the second chamber separates the solids from the liquids in the waste. Each subsequent chamber may be used as a previous chamber is filled with solids or the respective filter clogs. Accordingly, each chamber is utilized in succession, as needed, depending upon the amount of bodily waste, and solids therein, passed into the bodily waste collection device.

The systems and methods disclosed herein utilize a non-intrusive bodily waste collection apparatus having a plurality of chambers therein, a fluid collection container, and a vacuum source fluidly connected to the chamber (e.g., via the fluid collection container). Bodily waste collection devices, such as pouches or the like, may be fluidly connected to the bodily waste collection apparatus. The bodily waste collection device may be positioned on a patient or wearer to receive (e.g., directly) bodily waste from the patient. Accordingly, the bodily waste may travel from the bodily waste collection device to the bodily waste collection apparatus.

By filtering the liquid from the solids successively in each chamber, the liquid may be removed from the bodily waste separation device while the solids are retained. Accordingly, the volume of the bodily waste collected is reduced, thereby increasing the amount of time that the bodily waste separation device may be used as compared to a device having a single chamber and filter. The devices, systems, and methods disclosed herein also prevent clogging of drainage tubing used to remove the liquid from the bodily waste by filtering solids form the liquid. The bodily waste collection systems and methods are particularly effective for collecting semi-solid stool or liquid stool (e.g., diarrhea).

Figure 1:
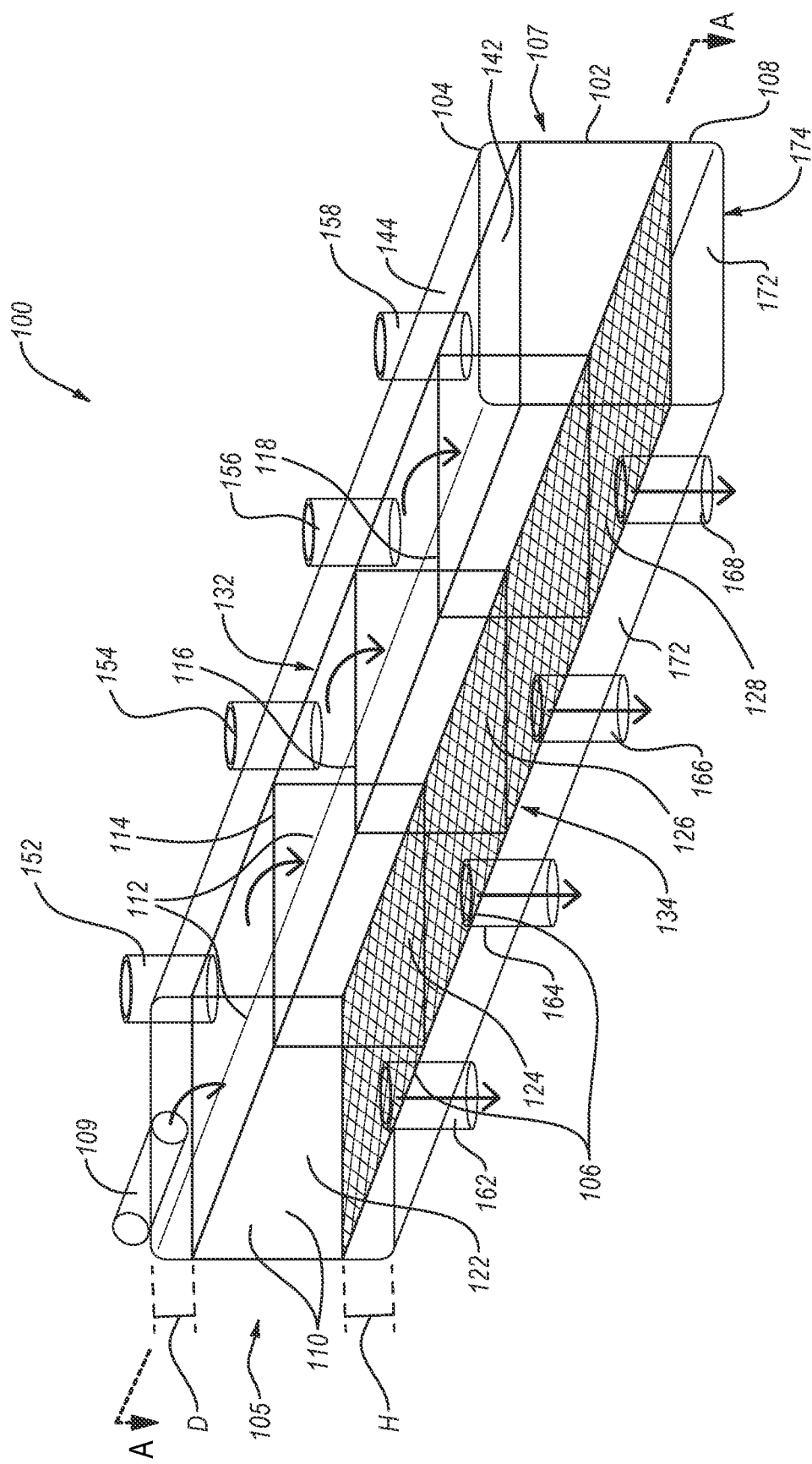
FIG. 1 is an isometric view of a bodily waste separation device, according to an embodiment.
Figure 2:
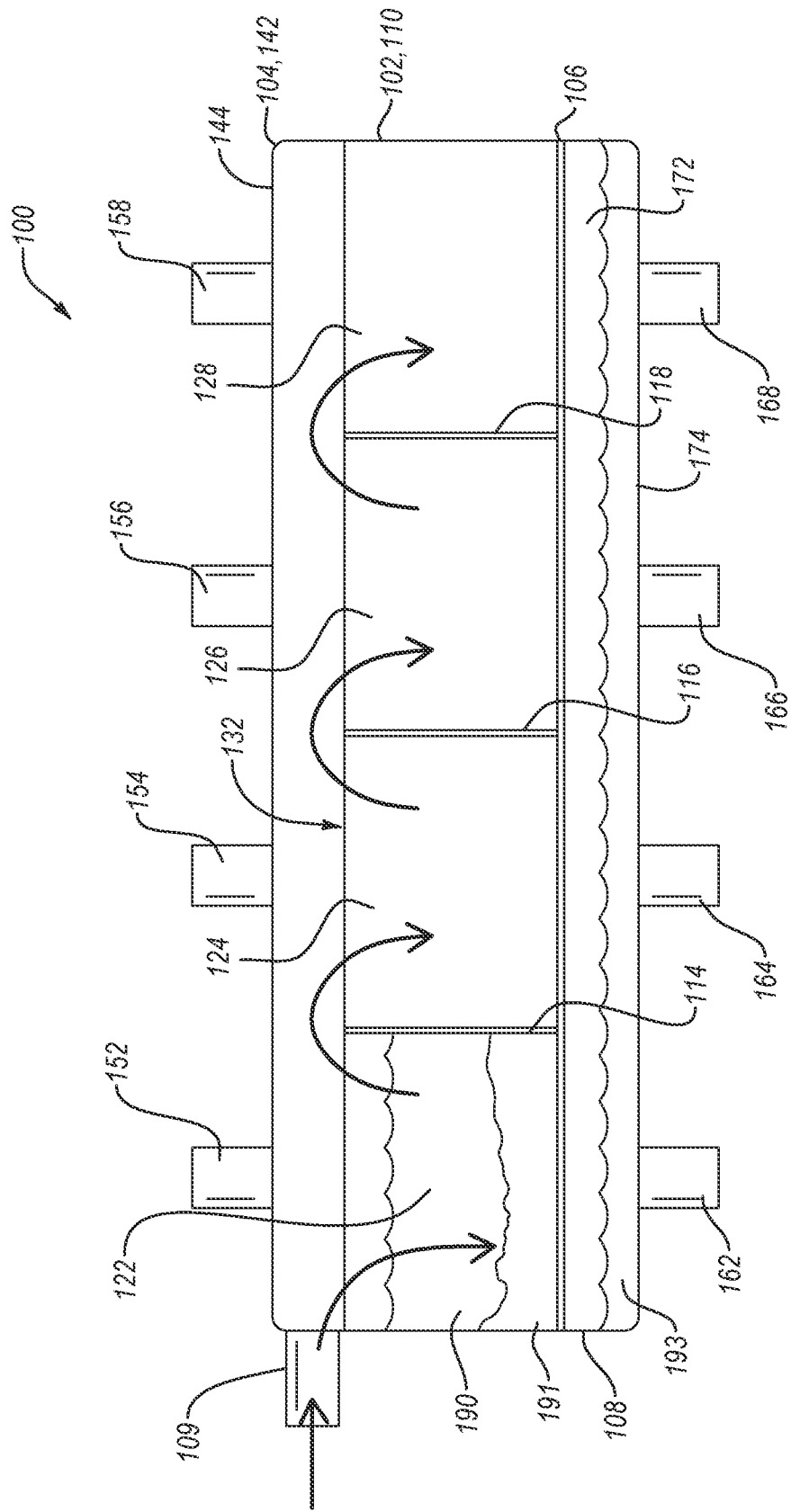
FIG. 2 is side view of the bodily waste separation device of FIG. 1.

FIG. 1 is an isometric view of a bodily waste separation device 100, according to an embodiment. FIG. 2 is side view of the bodily waste separation device 100 of FIG. 1. The device 100 includes an at least semi-rigid tray 102, a lid 104, a filter 106, and an output manifold 108. The lid 104 is positioned on top of the at least semi-rigid tray 102. The output manifold 108 is positioned below the at least semi-rigid tray 102. The filter 106 is positioned between the at least semi-rigid tray 102 and the output manifold 108. The bodily waste separation device 100 includes an intake 109. Bodily waste may be input into the bodily waste separation device 100 via the intake 109 in the first end region 105. Liquids may be removed from the bodily waste via the filter 106, leaving the solids in the bodily waste separation device 100. The liquids may be removed from the bodily waste separation device 100 via the output manifold 108, such as via one or more drainage ports therein.

The semi-rigid tray 102 includes at least semi-rigid outer walls 110 defining in interior region 112. The semi-rigid tray 102 includes a plurality of dividers 114, 116, and 118 disposed consecutively within the interior region 112 to form (e.g., divide the interior region into) a plurality of chambers 122, 124, 126, and 128 arranged consecutively between the outer walls 110. For example, the plurality of dividers 114, 116, and 118 are longitudinally spaced from each other consecutively along the longitudinal length of the interior region 112. Each of the dividers 114, 116, and 118 extend from one outer wall to another, opposite, outer wall to isolate portions of the interior region 112 thereby forming the plurality of chambers 122, 124, 126, and 128. For example, each of the plurality of dividers 114, 116, and 188 may extend from the outer wall 110 on a first side of the interior region 112 to the outer wall 110 on a second side of the of the interior region 112 to separate each chamber of the plurality of chambers 122, 124, 126, and 128.

The outer walls 110 have an upper end 132 and a lower end 134. The outer walls 110 are at least semi-rigid, such as being formed of a material that resists deformation under external forces. The dividers 114, 116, and 118 may also be at least semi-rigid. The dividers may also have an upper end and a lower end, where the lower end rests against the filter 106 and the upper end is spaced from an interior surface of the lid 104 to allow bodily waste to flow therebetween when the respective chamber fills with bodily waste. The inner surface of the outer walls 110 may include one or more slots into which the dividers 114, 116, and 118 may be disposed. In some examples, the lateral ends of the dividers 114, 116, and 118 may be adhered or welded to the inner surface of outer walls 110. The dividers 114, 116, and 118 may integrally formed with the outer walls 110. The dividers 114, 116, and 118 may be spaced from each other within the outer walls by at least 5 cm, such between 5 cm and 20 cm.

In some examples, the outer walls 110 and the may be formed of polymer(s) or glass. For example, the outer walls 110 may be formed of one or more polycarbonates, polyethylenes (e.g., HDPE), polyesters (e.g., polyethylene terephthalate), polypropylenes, polyether ether ketone ("PEEK"), fluoropolymers (e.g., polytetrafluoroethylene), polyvinyl chlorides, or the like. The outer walls 110 may have dimensions (e.g., thickness of at least 2 mm) and a material composition sufficient to render the outer walls 110 at least semi-rigid. For example, the outer walls 110 may include a rigid polymer. In some examples, at least a portion of the outer walls 110 may be transparent. The dividers 114, 116, and 118 may be formed of any of the materials disclosed herein for the outer walls 110.

The lid 104 may fit on the at least semi-rigid tray 102. For example, the lid 104 may be sized and shaped to fluidly seal to the upper end 132 of the outer walls 110. In some examples, the upper end 132 of the outer walls 110 may have an inward or outward lip sized to accommodate the lid 104, such as a lower end of the lid 104.

The lid 104 may include a body having sidewalls 142 and an upper surface 144. The bottom end of the lid 104 may be open. The sidewalls 142 may be dimensioned to space the upper surface 144 from the top of the dividers 114, 116, and 118 by a selected distance D. Accordingly, as the bodily waste fills a chamber (e.g., 122), the bodily waste may pass over the divider (e.g., 114) of the chamber (e.g., 122) into a subsequent chamber (e.g., 124). The distance D may be at least 1 cm, such as 1 cm to 15 cm, 2 cm to 10 cm, 1 cm to 5 cm, or less than 10 cm.

Figure 4:
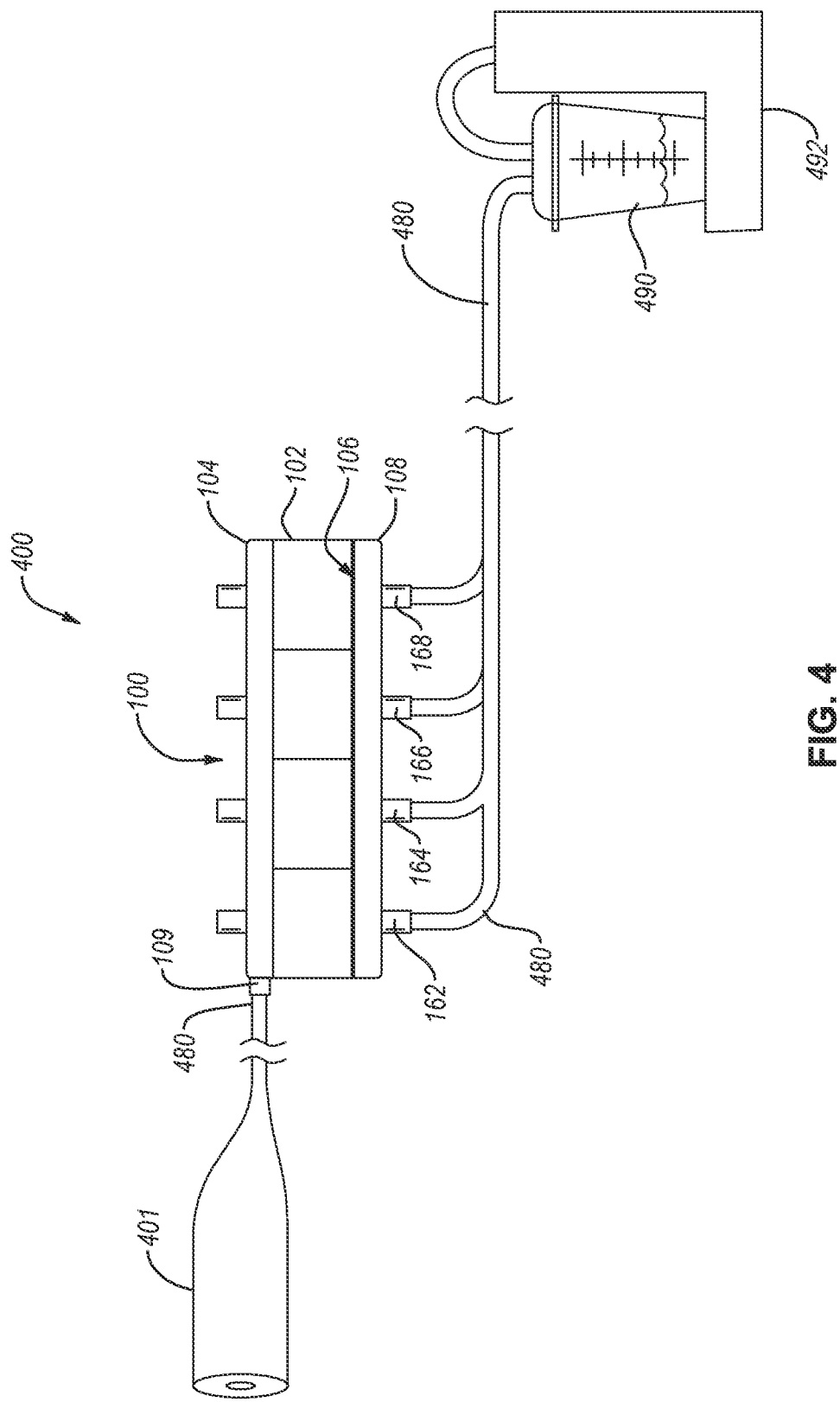
FIG. 4 is a schematic of a bodily waste collection system, according to an embodiment.

The lid 104 may include the intake 109 therein. The intake 109 may be disposed in the first end region 105. For example, the lid 104 may include an opening or conduit in the sidewalls 142 or the upper surface 144 in the first end region 105. The opening or conduit of the intake 109 is positioned to fluidly connect the interior region 112 with the outer environment or another device, such as a bodily waste collection device (FIG. 4). The intake 109 may be sized and shaped to allow bodily waste (e.g., at least partially liquid stool) to pass therethrough. In some examples, the intake 109 may be disposed one of the outer walls 110, such as at or near the upper end 132.

The lid 104 may be made of a material that is similar or identical to the material of the at least semi-rigid tray 102. For example, the lid 104 may be formed of a polymer or glass. In some examples, the material of the lid 104 may differ from the material of the tray 102, such as being different polymers or being a polymer when the tray includes glass.

In some examples, the lid 104 includes one or more access ports 152, 154, 156, or 158. The one or more access ports 152-158 may be disposed on the upper surface 144. The one or more access ports 152-158 may be a hole or conduit disposed on the lid 104, such as on the upper surface 144. The one or more access ports 152-158 may be sized and shaped to allow access to the interior region 112 from outside of the bodily waste separation device 100. For example, the one or more access ports 152-158 may be sized and shaped to allow a health care professional to insert a sample collection tool or syringe therethrough. The one or more access ports 152-158 may be re-sealable, such as having a plug. In some examples, the one or more access ports 152-158 may be operably coupled to medical tubing, such as medical tubing operably coupled to a fluid supply. In such examples, the fluid supply may be used to flush the interior region 112 with fluid (e.g., water or air). The lid 104 may include one access port. The lid 104 may include an access port for every chamber or every other chamber.

The filter 106 is disposed in the bottom of the chambers 122-128. The filter 106 is disposed between the lower end 134 of the outer walls 110 and the output manifold 108. For example, the filter 106 may be in contact with or sealed to the bottom end of the outer walls 110 and the dividers 114, 116, and 118. Accordingly, the chambers 122-128 are at least partially defined by the filter 106, the outer walls 110, and the dividers 114, 116, and 118.

The filter 106 includes an at least a semi-rigid sieve. For example, the filter may include a polymer, glass, or metal sieve having a selected sieve size. The material of the sieve may include any of the polymers disclosed herein, any glass, or any metal. The filter 106 may include one or more layers of a grate or mesh material, such as a single layer or dual layers. The filter 106 material may include a grate or fibers of a polymer, glass, or a natural material. For example, the grate or mesh material may include fibers of a polymer, such as nylon, polypropylenes, polyethylenes, polyethylene terephthalates, polystyrenes, polyurethanes, polycarbonates, polyamides, polyesters, polyacrylates, polychloroprene, vinyl, polyvinyl chloride, poly(vinyl imidazole), latex, silanes (e.g., an halogenated alkyl silane), perfluorinated polymers, polytetrafluoroethylene (PTFE), chlorosulphonate polyolefins, polyethylene oxide, blends or copolymers of any of the foregoing. The mesh may be formed of natural fibers such as cotton (e.g., cheesecloth). The mesh material may be woven or non-woven. The grate or mesh material may be molded.

The sieve size (e.g., mesh size) of the mesh or sieve of the filter 106 may include at least about a five micrometer (μm) mesh, such as about 5 μm to about 1,500 μm, about 100 μm to about 1000 μm, about 250 μm to about 500 μm, about 500 μm to about 1,000 μm, less than about 1,500 μm, less than about 1,000 μm, less than about 800 μm, less than about 400 μm, or larger than about 100 μm. As bodily waste is disposed in a chamber, the liquids therein may pass through the filter 106 and the solids therein may be retained by the filter 106. The filter 106 may be a single piece across all of the chambers or may be a plurality of filters 106 each disposed in a respective chamber.

The liquids that pass through the filter 106 move into the output manifold 108. The output manifold 108 may include a basin defined at least in part by one or more walls 172 and a lower surface 174. The one or more walls 172 may space the lower surface 174 from the filter 106 and the lower end of the one or more outer walls 110 by a selected height H. The height H may be at least 0.5 cm, such as 0.5 cm to 15 cm, 2 cm to 10 cm, 1 cm to 5 cm, or less than 10 cm. The output manifold 108 may function as a sump having a volume defined in part by the height H of the one or more walls 172.

The one or more walls 172 of the output manifold 108 may be sized and shaped to engage (e.g., fluidly seal to) the one or more outer walls 110 of the tray 102. For example, one or more of an upper end of the one or more walls 172 of the output manifold or the lower end 134 of the outer walls 110 may have an inward or outward lip sized to accommodate a corresponding one of the lower end 134 of the outer walls 110 or the one or more walls 172 of the output manifold 108. The one or more walls 172 of the output manifold 108 may be parallel or coplanar with the one or more outer walls 110.

The output manifold 108 may be formed of any of the materials disclosed herein for the outer walls 110. For example, the output manifold 108 may be at least semi-rigid. One or more portions of the output manifold 108 may be transparent.

The output manifold 108 may include one or more drainage ports 162, 164, 166, and 168. One or more drainage ports 162-168 may be disposed on the lower surface 174 or the one or more walls 172. The one or more drainage ports 162-168 may include holes or conduits sized and shaped to fluid connect to one or more drainage tubes. While shown as having four drainage ports 162-168, example bodily waste separation devices may include any number of drainage ports, such as one drainage port, one drainage port per chamber, one drainage port per two chambers, or the like. The liquid that is filtered from the bodily waste in the respective chambers through the filter 106 into the output manifold 108 may be removed from the interior region 112 via the one or more drainage ports 162-168 using gravity or vacuum pressure.

Referring to FIG. 2, bodily waste (e.g., liquid 190 and solid 191) is deposited and filtered in the bodily waste separation device 100. As liquid 190 drains from the bodily waste, the solids 191 begin to fill the chamber 122 and/or the filter 106 may be occluded by the solids 191. Accordingly, chamber 122 may begin to fill with bodily waste, which may spill over the divider 114 into chamber 124, where a clear section of the filter 106 (or even separate filter) may be positioned. Accordingly, the bodily waste in chamber 124 may be filtered to separate the liquid 190 from the solids 191 therein. Each successive chamber 126 and 128 may be utilized as a previous chamber is filled in the same manner.

As noted above, the tray 102, the lid 104, the filter 106, and the output manifold 108 may be at least semi-rigid. Such rigidity allows the components of the bodily waste separation device 100 to maintain a connection and seal between each other to prevent leakage of bodily waste or components thereof from the bodily waste separation device 100. Accordingly, in some examples, one or more of the components may be rigid, such as having substantially no deformation when subjected to an external force (e.g., compressed or bumped by a health care professional or the patient) or when the interior region 112 is placed under vacuum.

While shown as having three dividers 114, 116, 118 and four chambers 122-128, example bodily waste filtration devices may have any number of dividers and chambers. For example, bodily waste collection devices may include one divider and two chambers, two dividers and three chambers, or four dividers and four chambers.

In some examples, the components of the bodily waste separation device may have different configurations than those shown in FIGS. 1 and 2. For example, the corners and edges of the device 100 may be rounded so as to prevent discomfort when disposed next to a patient during use. While shown as being cuboid in FIGS. 1 and 2, the bodily waste separation device (and components thereof) may be any shape such as prismatic, round, domed, cupped, cylindrical, or the like. The components of the bodily waste separation device may vary in size or shape. For example, the lid may not have sidewalls or the output manifold may not have sidewalls.

Figure 3:
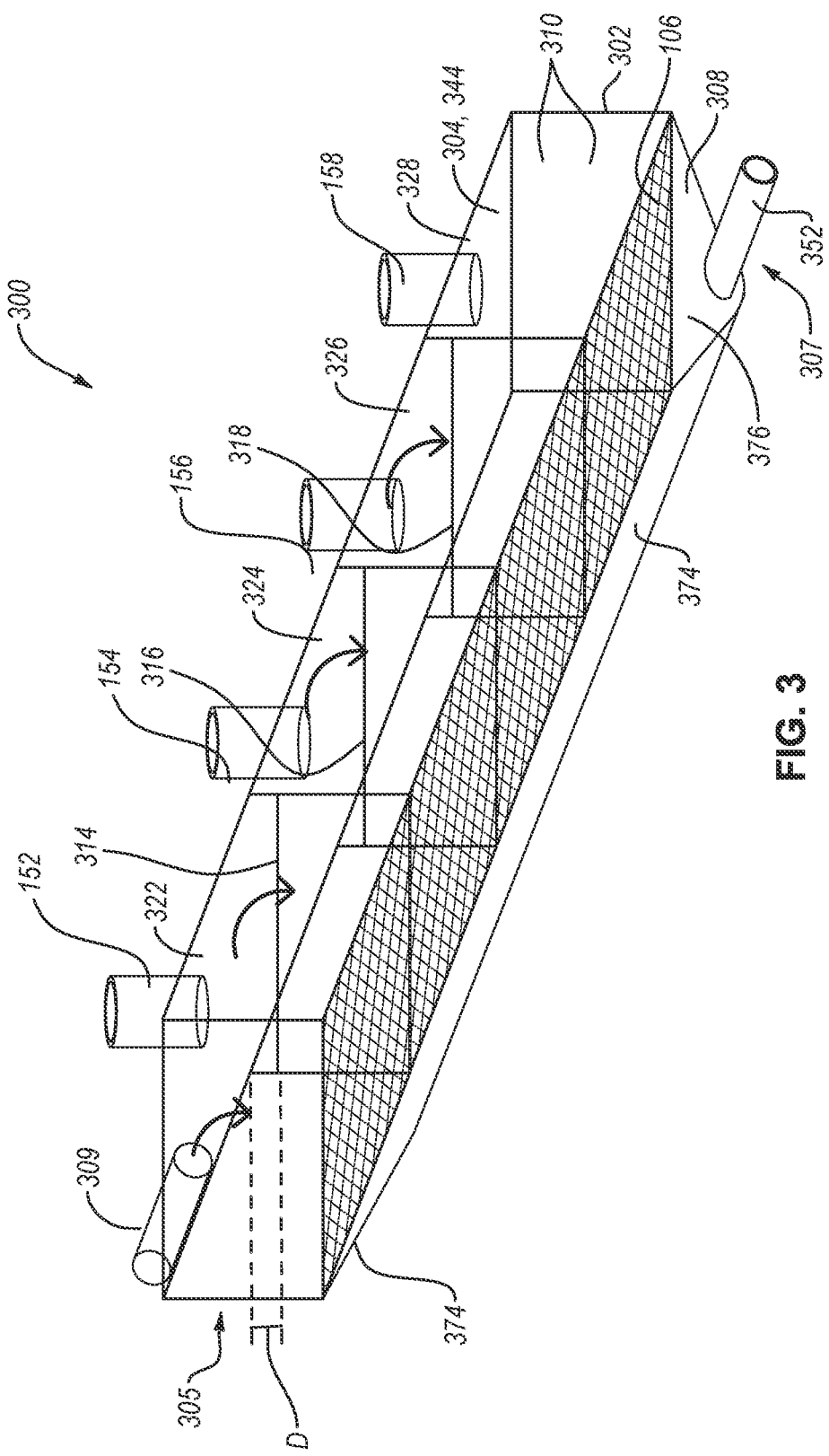
FIG. 3 is an isometric view of a bodily waste separation device, according to an embodiment.

FIG. 3 is an isometric view of a bodily waste separation device 300, according to an embodiment. The bodily waste separation device 300 includes an at least semi-rigid tray 302, a lid 304, a filter 106, and an output manifold 308. The lid 304 and the output manifold 308 may not include sidewalls. The semi-rigid tray 302 may be similar or identical to the semi-rigid tray 102 in one or more aspects. For example, the semi-rigid tray 302 may include one or more outer walls 310 that are similar or identical to the one or more outer walls 110, in one or more aspects. The semi-rigid tray 302 may include dividers 314, 316, and 318, which may be similar or identical to the dividers 114, 116, and 118, in one or more aspects. For example, the dividers 314, 316, and 318 may be formed of an at least semi-rigid material. The height of the dividers 314, 316, and 318 may be less than the height of the outer walls 310.

The intake 309 may be similar or identical to the intake 109 in one or more aspects. For example, the intake 309 may be sized and shaped as a hole, port, or other connection to fluidly coupled to a conduit. As shown, the intake 309 may be disposed on one of the outer walls 310 of the tray 302, such as in the first end region 305 of the bodily waste separation device. The intake 309 may place the interior region of the bodily waste separation device 300 in fluid communication with another device or the environment outside of the bodily waste separation device 300. The intake 309 may be located nearest the upper end of the outer wall 310 to allow maximum usage of the chamber 322. In some examples, the intake may be disposed on the lid 304 in communication with the chamber 322.

The lid 304 may be similar or identical to the lid 104, in one or more aspects. For example, the lid 304 may include an upper surface 344 having one or more access ports 152, 154, 156, and 158 disposed thereon. The upper surface 344 may be similar or identical to the upper surface 144 in one or more aspects. In contrast to the lid 104, the lid 304 may not include sidewalls. Accordingly, the lid 304 may sit substantially flush with the upper end of the outer walls 310. Due to the difference in height between the outer walls 310 and the dividers 314, 316, and 318, bodily waste may flow over the dividers 314, 316, and 318 even when the lid 304 is disposed on the tray 302. The difference in height may be the distance D as disclosed above.

The filter 106 is positioned on the lower end of the outer walls 310 of the tray 302 as disclosed above with respect to the bodily waste separation device 100 above.

The output manifold 308 may be similar or identical to the output manifold 108 in one or more aspects. For example, the output manifold 308 includes one or more drainage ports 352 and may be constructed of any of the at least semi-rigid materials disclosed herein. In contrast to the output manifold 108, the output manifold 308 may not include sidewalls. For example, the output manifold 308 may include the lower surface 374 and the end surfaces 376. The lower surface may extend from the lower end of the outer walls 310 to form a trough or basin under the filter 106. In some examples, the lower surface 374 may be a rounded, pyramidal, or the like. Accordingly, the liquids collected in the output manifold 308 may be directed toward a central, lowermost portion of the output manifold 308.

The end surfaces 376 may be disposed on the lower surface 374 of the first and second end regions 305 and 307 of the bodily waste separation device 300. The end surfaces 376 may be co-planar with the outer walls 310 in the first and second end regions or may be obliquely angled (e.g., pyramidal with the lower surface 374) thereto as shown. In some examples, the end surfaces 376 may be a portion of the lower surface 374, such as in a substantially domed configuration.

The output manifold 308 includes one or more drainage ports 352. The one or more drainage ports 352 may be similar or identical to any of the drainage ports disclosed herein, in one or more aspects. For example, the drainage port 352 may include a port, a hole, or attachment for coupling drainage tubing thereto. The drainage port 352 may be disposed on the end surface 376 in the second end region of the bodily waste separation device 300, such as on the opposite of the bodily waste separation device 300 from the intake 309. The drainage port 352 may be disposed on the end surface 376 or the lower surface 374 at a portion thereof expected to sit at or near a gravimetrically low point in the output manifold 308 while the bodily waste separation device 300 is used. Accordingly, liquids may be directed to the low point and drained therefrom via the drainage port 352.

In some examples (not shown), the bodily waste separation device 300 may include feet, outriggers, or other features to prevent the bodily waste separation device 300 from tipping to one side about the apex of the lower surface 374.

While shown as being substantially prismatic (e.g., box shaped) in FIGS. 1-3, other examples may utilize different shaped devices such as round, domed, cupped, triangular prismatic, etc. For example, a round or any other shaped device may include a plurality of concentrically arranged chambers having concentrically arranged dividers therebetween. Such examples may have an intake at an innermost chamber and at least one drainage port at an outermost chamber, or vice versa.

The bodily waste separation devices disclosed herein may be used in a system for collecting bodily waste. FIG. 4 is a schematic of a bodily waste collection system 400, according to an embodiment. The bodily waste collection system 400 includes a fluid storage container 490 configured to hold a fluid, bodily waste separation device 100 fluidly connected to the fluid storage container 490, and a vacuum source 492 fluidly connected to one or more of the fluid storage container 490 or the bodily waste separation device 100. Accordingly, the bodily waste collection system 400 may be used to collect bodily waste (e.g., at least semi-liquid stool) from a patient (e.g., user) and filter the liquids from the bodily waste while retaining the solids within the bodily waste separation device 100. The bodily waste separation device 100 may be fluidly connected to one or more of the bodily waste collection device 401, the fluid storage container 490, or the vacuum source 492 via drainage tubing 480. The system 400 may include a controller (not shown) to selectively control operation of the vacuum source 492.

The bodily waste collection device 401 includes a fluid impermeable barrier configured to receive and hold bodily waste from an anus or stoma of a patient. The bodily waste collection device 401 may include an annular body for interfacing with a patient, a fluid impermeable barrier for retaining bodily waste therein, and one or more ports for draining bodily waste received via the annular body. Example bodily waste collection devices may include pouches, bags, or the like. The bodily waste collection devices 401 may include a non-intrusive bodily waste collection devices such, such as those disclosed in U.S. Provisional Patent Application No. 63/033,310, filed on 2 Jun. 2020, the disclosure of which is incorporated herein, in its entirety, by this reference. The annular body may include a wafer of fluid impermeable material with an attachment feature such as adhesive thereon to attach the annular body round the anus or stoma of the wearer. The fluid impermeable barrier may be formed from a fluid impermeable material, such as portions (e.g., layers) including a polymer, a metal film, rubber, or the like. For example, the fluid impermeable barrier may include silicone, polypropylenes, polyethylenes, polyethylene terephthalates, polystyrenes, polyurethanes, polycarbonates, polyamides, polyesters, polyacrylates, polychloroprene, vinyl, polyvinyl chloride, poly(vinyl imidazole), latex, silanes (e.g., an halogenated alkyl silane), perfluorinated polymers, polytetrafluoroethylene (PTFE), chlorosulphonate polyolefins, polyethylene oxide, blends or copolymers of any of the foregoing, or any other fluid impermeable polymer. The fluid impermeable barrier may be transparent in one or more portions thereof. The fluid impermeable barrier may be translucent or opaque in one or more portions thereof. The bodily waste collection devices 401 may include intrusive bodily waste collection devices such as ostomy bags, rectal tubes/catheters, intra anal stool bags, or the like.

The bodily waste collection device 401 may be attached to a wearer to collect the waste from the wearer. For example, device 401 may have an opening sized and shaped to be disposed in, on, or around the wearer's anus or stoma for use. Waste enters the bodily waste collection device 401, and may be contained therein for removal to the bodily waste separation device 100 such as via the drainage tubing 480 and intake 109. The bodily waste collection device 401 is fluidly connected to the bodily waste separation device 100 via the intake 109. The bodily waste may move from the device 401 to the bodily waste separation device 100 via gravity or by vacuum force. For example, a vacuum introduced in the bodily waste separation device 100 via the vacuum source 492 may be communicated into the bodily waste collection device 401 through the bodily waste separation device 100.

The drainage tubing 480 (e.g., drainage tube) of the system 400 may include medical tubing. For example, the drainage tubing 480 may be constructed of one or more polymers such as silicone, latex, ethylene vinyl acetate (EVA), polytetrafluoroethylene (PTFE), silicone polyurethane, polyamide, polyurethane, polyethylene, other thermoplastics and block copolymers thereof, or any other suitable polymers for medical use.

The drainage tubing 480 may fluidly connect the bodily waste collection device 401 to the bodily waste separation device 100. In some examples, the bodily waste collection device 401 may be fluidly connected directly to the bodily waste separation device 100. In either case, bodily waste collected in the bodily waste collection device 401 may be moved into the bodily waste separation device 100.

While shown as the bodily waste separation device 100, any bodily waste separation device may be used in the system 400. As liquids are filtered from the bodily waste in the bodily waste separation device 100, the liquid may be collected in the output manifold 108 thereof and removed therefrom via the drainage tubing 480.

For example, the drainage tubing 480 fluidly connect the fluid storage container 490 with the bodily waste separation device 100, such as via the one or more drainage ports 162-168. Drainage tubing 480 may include drainage tubing corresponding to each chamber of the plurality of chambers, every other chamber of the plurality of chambers, or only one for all of the plurality of chambers in the bodily waste separation device 100. Drainage tubing spanning from the bodily waste separation device 100 to the fluid storage container 490 may be referred to at output conduits or tubing. The fluids (e.g., liquid from bodily waste and any gasses produced from the bodily waste) may be removed from the bodily waste separation device 100 via the drainage tubing 480. The fluids may travel through the drainage tubing 480 to the fluid storage container 490, such as via vacuum force. The drainage tubing 480 from multiple drainage ports 162-168 may be joined into single piece of drainage tubing 480 via one or more junction connections (e.g., T-joints, maniflolds, or the like). The junction connections may include male or female connections for mating to the drainage tubing 480.

Fluid storage container 490 may include a bag (e.g., drainage bag), a bottle or canister (e.g., collection jar), or any other enclosed container for storing bodily fluids. The vacuum source 492 may be fluidly coupled to one or more of the fluid storage container 490 or the bodily waste collection device via the drainage tubing 480.

The vacuum source 492 may apply a vacuum to directly or indirectly draw fluid(s) from the interior region of the bodily waste separation device 100, via the drainage tubing 480. For example, the vacuum source 492 may provide a vacuum for one or more of pulling bodily waste from the bodily waste collection device 401 into the bodily waste separation device 100 or pulling fluids from the bodily waste separation device 100 into the fluid storage container 490. The fluid collected from the bodily waste separation device 100 is moved through the drainage tubing 480 into the fluid storage container 490.

The vacuum source 492 may be fluidly connected to the fluid storage container 490 by a drainage tubing 480 and the fluid storage container 490 may be fluidly connected to the bodily waste separation device 100 via one or more additional sections of drainage tubing 480. By having a separate connection to the vacuum source 492 on the fluid storage container 490, the fluids removed from the bodily waste separation device 100 may be prevented from entering the vacuum source 492.

The vacuum source 492 may include one or more of a manual vacuum pump, an electric vacuum pump, a wall pump, a diaphragm pump, a centrifugal pump, a displacement pump, a magnetically driven pump, a peristaltic pump, or any pump configured to produce a vacuum. The vacuum source 492 may include a wall mounted suction line, such as found in a hospital room. The vacuum source 492 provides a vacuum or suction to remove fluid from the bodily waste separation device 100. In examples, the vacuum source 492 may be powered by one or more of a power cord (e.g., connected to a power socket), one or more batteries, or even manual power (e.g., a hand operated vacuum pump). The vacuum source 492 may include one or more of a switch, a button, a plug, a remote, or any other actuator suitable to activate the vacuum source 492. The vacuum source 492 may be selectively operated by a user (e.g., medical personnel, the wearer, or a caretaker), such as directly on the vacuum source 492 or via a controller (not shown).

The bodily waste separation device 100 may be fluidly connected to an input source, such as via the access ports. For example, the bodily waste separation device 100 may fluidly connected to the input source via one or more input conduits (not shown) operably coupled thereto. The input conduits may be similar or identical to the drainage tubing 480 in one or more aspects. The input source may be used to input one or more fluids into one or more of the chambers of the bodily waste separation device 100. For example, the input source (e.g., gas or air source) may be used to periodically input fluid into the chambers to flush the chambers. The input source may include one or more of an air pump, a compressed air line, an oxygen source (e.g., compressed oxygen), a nitrogen source (e.g., compressed nitrogen), or any other source of gas. The input source may include one or more of a liquid source such as a water line, water pump, a saline pump, or the like. The input source may be used to selectively input a liquid (e.g., saline) or gas into the chambers of the bodily waste separation device 100 to clean the chambers or flush the chambers. In some examples, the input source may include an air pump, a wall pump, a compressor, an air line (e.g., in a hospital room), or the like. In some examples, the input source may include a liquid (e.g., water) pump, a water line, or the like. In examples, where the fluid includes a liquid, the input source may include a heater or temperature control component to control the temperature of the liquid pumped into the bodily waste separation device 100.

In some examples, the input source and the vacuum source 492 may be located in a single device, such as a combination pump, diaphragm pump, or any other pump capable of creating a vacuum and pressurized air.

The bodily waste separation devices disclosed herein may include one or more vents or one-way valves such as on the lid or outer walls. Such one-way valves may be sized and shaped to open inwardly toward the chamber 126 responsive to a vacuum force applied thereto. Accordingly, vacuum applied in the chamber 126 may be at least partially prevented from reaching the patient by traveling up the system 400 through the bodily waste collection device.

Figure 5:
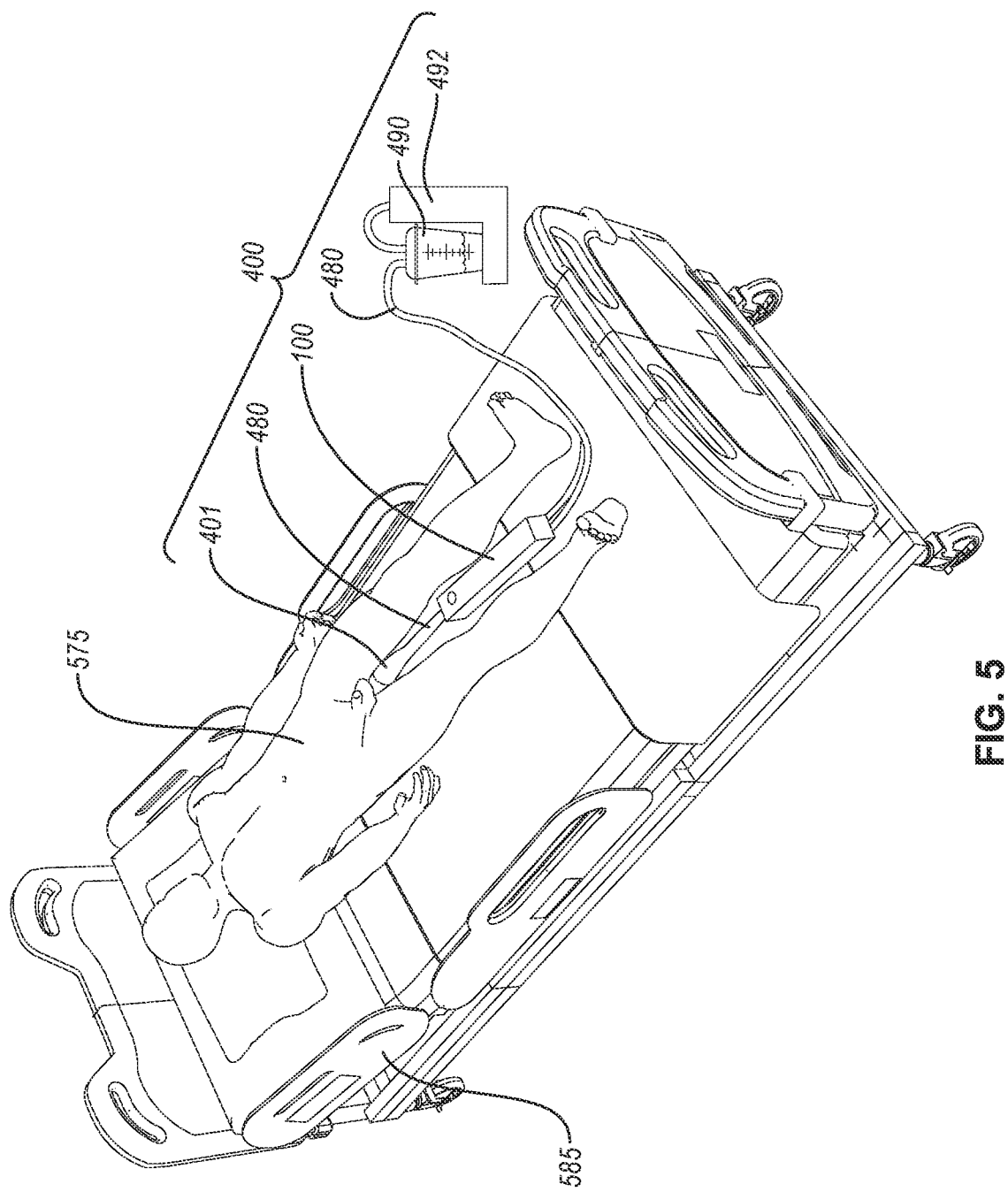
FIG. 5 is a schematic of the bodily waste collection system during use, according to an embodiment.

FIG. 5 is a schematic of the bodily waste collection system 400 during use, according to an embodiment. The bodily waste collection system 400 includes the bodily waste collection device 401, the fluid storage container 490, and the vacuum source 492. One or more portions of drainage tubing 480 may fluidly connect one or more components of the system 400. The bodily waste separation device 100 may be similar or identical to any of the bodily waste separation devices 100 disclosed herein, in one or more aspects. The bodily waste collection device 401 may be similar or identical to any of the bodily waste collection devices disclosed herein.

During use, one or more portions of the system 400 may be disposed between the legs of a patient 575. The bodily waste collection device 401 may be disposed between the legs of the user, such as resting on a hospital bed 585. The bodily waste separation device 100 may disposed on the bed 585. In some examples, one or more of the bodily waste separation device 100, the fluid storage container 490, and the vacuum source 492 may be disposed on or below the bed 585, such as to use gravity to move the bodily waste through the system 400.

The bodily waste collection device 401 may be positioned in contact with the patient 575, such as within the gluteal cleft of the patient 575. An opening (not shown) of the bodily waste collection device 401 may be positioned around the anus of the patient 575. At least a portion of the bodily waste collection device 401 may be retained within the gluteal cleft of the patient 575. For example, an annular body of a bodily waste collection device 401 may be adhered to the skin of the patient 575 around the anus and when the patient's (e.g., wearer's) legs are closed, the annular body will be deformed (e.g., folded) in the gluteal cleft.

As the patient 575 has bowel movements, the waste (e.g., stool) is collected in bodily waste collection device 401 via the opening. The waste may move into the bodily waste separation device 100 from the bodily waste collection device 401, such as via gravity or vacuum. The liquids are filtered form the solids in the bodily waste separation device 100.

The solids are retained in the chambers within the bodily waste separation device 100 while liquid drains from the waste and passes out of the output manifold into the fluid storage container 490. Such drainage may be accomplished by one or more of gravity or the vacuum applied in the interior region (e.g., chambers) of the bodily waste separation device 100 by the vacuum source 492. The liquid is removed from the chamber via the one or more drainage ports and the drainage tubing 480. The liquid is deposited in the fluid storage container 490. The vacuum source 492 may be intermittently controlled to apply a vacuum at selected intervals.

An input source (not shown) may be used to periodically input fluid into the chambers, such as to clean the chambers. The input source may input one or more fluids into the bodily waste separation device 100 via the access port(s) and the input conduits. In some examples, a stream of air or liquid may be passed into the one or more chambers from the input source to flush or clean the same. The fluid may be provided while the vacuum is being applied or while the vacuum is not being applied.

Figure 6:
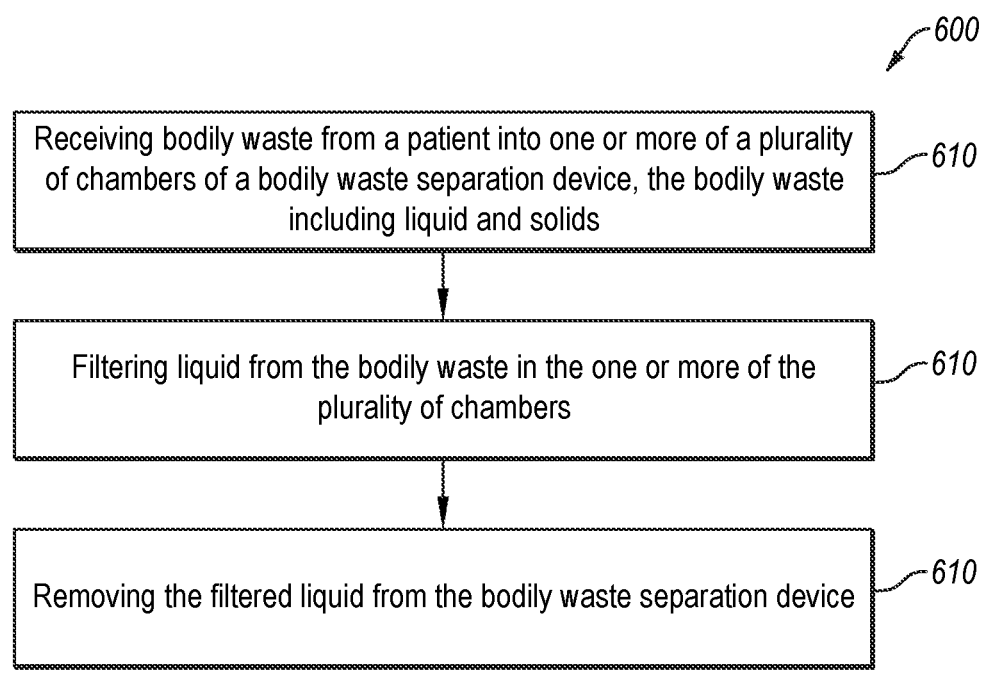
FIG. 6 is a flow diagram of a method to collect bodily waste, according to an embodiment.

FIG. 6 is a flow diagram of a method 600 to collect bodily waste, according to an embodiment. The method 600 includes block 610, which recites "receiving bodily waste from a patient into one or more of a plurality of chambers of a bodily waste separation device, the bodily waste including liquid and solids." Block 610 may be followed by block 620, which recites "filtering liquid from the bodily waste in the one or more of the plurality of chambers." Block 620 may be followed by block 630, which recites "removing the filtered liquid from the bodily waste separation device." Blocks 610, 620, and 630 of the method 600 are for illustrative purposes. For example, the blocks may be modified, supplemented, split, or combined. In an example, one or more of the blocks 610, 620, or 630 may be omitted from the method 600. Additional blocks may be included. Any of the blocks 610, 620, or 630 may include using any of the bodily waste separation devices, bodily waste collection devices, or systems disclosed herein.

Block 610 recites "receiving bodily waste from a patient into one or more of a plurality of chambers of a bodily waste separation device, the bodily waste including liquid and solids." The bodily waste collection separation or components thereof may be similar or identical to any of the bodily waste separation devices disclosed herein, in one or more aspects. For example, the bodily waste collection device may include one or more of an at least semi rigid tray, a lid fluidly sealed to the at least semi-rigid tray, a filter bag, an intake configured to fluidly connect an interior region of the interior region to a bodily waste collection device, an output manifold fluidly sealed to the tray having one or more drainage ports sized and shaped to fluidly connect to one or more drainage tubes, and a filter disposed between the lower end of the outer walls and the output manifold. The at least semi-rigid tray may include at least semi-rigid outer walls defining an interior region, the outer walls having an upper end and a lower end and a plurality of dividers disposed consecutively within the interior region to form the plurality of chambers arranged consecutively between the outer walls.

Receiving bodily waste into one or more of a plurality of chambers of a bodily waste separation device may include receiving the bodily waste from a bodily waste collection device operably coupled to the bodily waste separation device. The bodily waste collection device may be similar or identical to any of the bodily waste collection devices disclosed herein. For example, the bodily waste collection device may include a fluid impermeable barrier configured to receive and contain bodily waste, such as from an anus or stoma of the patient.

The bodily waste separation device may form part of a bodily waste collection system. The bodily waste collection system may include any of the bodily waste collection systems disclosed herein. For example, the bodily waste collection system a fluid storage container fluidly connected to the bodily waste separation device and a vacuum source fluidly connected to one or more of the fluid storage container or the bodily waste separation device. The vacuum source may apply a vacuum to draw fluids from the interior region of the bodily waste separation device.

Receiving bodily waste into one or more of a plurality of chambers of a bodily waste separation device may include sequentially receiving the bodily waste in the plurality of chambers as each subsequent chamber fills with the solids from the bodily waste.

Block 620 recites "filtering liquid from the bodily waste in the one or more of the plurality of chambers." Filtering liquid from the bodily waste in the one or more of the plurality of chambers may include may include retaining the solids in the one or more of the plurality of chambers. Filtering liquid from the bodily waste in the one or more of the plurality of chambers may include applying a vacuum into the bodily waste separation device or utilizing gravity to drain liquid from the bodily waste.

Filtering liquid from the bodily waste in the one or more of the plurality of chambers may include filtering the liquid from the solids using the filter in the one or more of the plurality of chambers. Filtering liquid from the bodily waste in the one or more of the plurality of chambers may include collecting the liquid in an output manifold of the bodily waste collection device. Filtering liquid from the bodily waste in the one or more of the plurality of chambers may include retaining the solids within the one or more of the plurality of chambers.

Block 630 recites "removing the filtered liquid from the bodily waste separation device." Removing the filtered liquid from the bodily waste separation device includes draining the liquid from the output manifold of the bodily waste separation device, such as via gravity or vacuum force. Removing the filtered liquid from the bodily waste separation device includes draining the liquid using one or more drainage ports in the bodily waste separation device. For example, removing the filtered liquid from the bodily waste separation device may include applying a vacuum into the bodily waste separation device via the one or more drainage ports using the vacuum source.

Removing the filtered liquid from the bodily waste separation device may include depositing the filtered liquid in the fluid storage container.

The method 600 may include positioning an opening of the bodily waste collection device over the anus or stoma of the patient. Positioning the opening of the bodily waste collection device over the anus or stoma of a patient may include positioning the opening over the anus or stoma such that the opening at least partially (e.g., completely) encircles the anus or stoma. Accordingly, bodily waste passed through the anus or stoma may pass through the opening into the bodily waste collection device. Positioning the opening of the bodily waste collection device over the anus or stoma of a patient may include adhering the annular body of the bodily waste collection device to the patient, such as in the intergluteal cleft of the patient. The patient or a user (e.g., caretaker, medical professional, etc.) may position the opening of the bodily waste collection device over the anus or stoma of a wearer.

The method 600 may further include receiving waste from the anus or stoma into the bodily waste collection device. For example, receiving waste from the anus or stoma into the chamber includes receiving the waste into an inner region of the bodily waste collection device via the opening.

The method 600 may include applying a vacuum in the bodily waste collection device. Applying a vacuum to the bodily waste collection device may include utilizing any of the vacuum sources disclosed herein. Applying vacuum in the bodily waste collection device may include applying the vacuum via the bodily waste separation device. Applying a vacuum in the bodily waste collection device may include at least some of the bodily waste in the bodily waste collection device via a drainage tube disposed between the bodily waste collection device and the bodily waste separation device. Applying vacuum in the bodily waste collection device may include applying the vacuum via the fluid storage container.

In some examples, the method 600 may include measuring the fluid(s) that are removed from the bodily waste separation device, such as in the fluid storage container.

In some examples, the method 600 may include changing the bodily waste collection device for a new bodily waste collection device. In some examples, the method 600 may include changing the bodily waste separation device for a new fluid separation device. Such a change may be responsive to visually confirming that one or more of the plurality of chambers are filled to a point where a change of separation devices is desired, such as confirming via viewing the chambers through transparent outer walls.

Any of the example systems disclosed herein may be used to carry out any of the example methods disclosed herein, such as using a controller.

The useful life of the bodily waste separation devices may be lengthened by removing the fluids from the bodily waste received therein, which is possible by retaining the solids from the waste within the one or more chambers.

While various aspects and embodiments have been disclosed herein, other aspects and embodiments are contemplated. The various aspects and embodiment disclosed herein are for purposes of illustration and are not intended to be limiting. Features from any of the disclosed embodiments may be used in combination with one another, without limitation.

What is claimed is:

1. A bodily waste separation device, comprising:
   an at least semi-rigid tray, the at least semi-rigid tray including:
   at least semi-rigid outer walls defining an interior region, the at least semi-rigid outer walls having an upper end and a lower end;
   a plurality of dividers disposed consecutively within the interior region to form a plurality of chambers arranged consecutively between the at least semi-rigid outer walls; and
   a lid fluidly sealed to an upper end of the at least semi-rigid outer walls;
   an intake configured to fluidly connect the interior region to a bodily waste collection device;

an output manifold fluidly sealed to the at least semi-rigid outer walls at the lower end, the output manifold including one or more drainage ports configured to fluidly connect to one or more drainage tubes; and a filter disposed between the lower end of the at least semi-rigid outer walls and the output manifold, wherein the filter includes at least a semi-rigid sieve.

2. The bodily waste separation device of claim 1 wherein the at least semi-rigid outer walls include a rigid polymer.

3. The bodily waste separation device of claim 1 wherein at least a portion of the at least semi-rigid outer walls are transparent.

4. The bodily waste separation device of claim 1 wherein each of the plurality of dividers extend from the at least semi-rigid outer walls on a first side of the interior region to the at least semi-rigid outer walls on a second side of the of the interior region to separate each chamber of the plurality of chambers.

5. The bodily waste separation device of claim 1 wherein the lid includes one or more access ports.

6. The bodily waste separation device of claim 5 wherein the lid includes a body having one or more sidewalls and an upper surface, the upper surface being spaced from the at least semi-rigid outer walls of the tray by the sidewalls, and the one or more access ports are disposed on the upper surface.

7. The bodily waste separation device of claim 6 wherein the output manifold includes a basin having walls and a lower surface, the lower surface being separated from the filter and the lower end of the one or more sidewalls by the walls.

8. The bodily waste separation device of claim 7 wherein the one or more drainage ports are disposed in the lower surface.

9. The bodily waste separation device of claim 1 wherein the one or more drainage ports include a drainage port for each chamber.

10. The bodily waste separation device of claim 1 wherein the intake is disposed on the lid or one of the at least semi-rigid outer walls.

11. A bodily waste collection system, comprising:
a fluid storage container configured to hold a fluid;
a bodily waste separation device fluidly connected to the fluid storage container, the bodily waste separation device including:
an at least semi-rigid tray, the at least semi-rigid tray including:
at least semi-rigid outer walls defining an interior region, the at least semi-rigid outer walls having an upper end and a lower end;
a plurality of dividers disposed consecutively within the interior region to form a plurality of chambers arranged consecutively between the at least semi-rigid outer walls; and
a lid fluidly sealed to an upper end of the at least semi-rigid outer walls;
an intake configured to fluidly connect the interior region to a bodily waste collection device;
an output manifold fluidly sealed to the at least semi-rigid outer walls at the lower end, the output manifold including one or more drainage ports configured to fluidly connect to one or more drainage tubes; and
a filter disposed between the lower end of the at least semi-rigid outer walls and the output manifold, wherein the filter includes at least a semi-rigid sieve; and
a vacuum source fluidly connected to one or more of the fluid storage container or the bodily waste separation device, the vacuum source configured to apply a vacuum to draw fluid from the interior region.

12. The bodily waste collection system of claim 11, further comprising the bodily waste collection device, wherein the bodily waste collection device includes a fluid impermeable barrier configured to receive and hold bodily waste from an anus or stoma of a patient, and wherein the bodily waste collection device is fluidly connected to the bodily waste separation device via the intake.

13. The bodily waste collection system of claim 11, further comprising additional drainage tubing fluidly coupling the fluid storage container to the bodily waste separation device.

14. The bodily waste collection system of claim 13 wherein the additional drainage tubing includes an drainage tubing corresponding to each chamber of the plurality of chambers.

15. The bodily waste collection system of claim 11 wherein the vacuum source is fluidly connected to the fluid storage container.

16. The bodily waste collection system of claim 11 wherein the bodily waste collection device includes one or more access ports disposed therein.

17. The bodily waste collection system of claim 16 wherein the one or more access ports are disposed on the lid.

18. The bodily waste collection system of claim 16, further comprising one or more input conduits operably coupled to the one or more access ports.

19. The bodily waste collection system of claim 18 wherein the one or more input conduits are operably coupled to a fluid source.

* * * * *